United States Patent [19]

Danos

[11] 4,229,651

[45] Oct. 21, 1980

[54] RADIATION SCANNING METHOD AND APPARATUS

[76] Inventor: Michael Danos, 407 Muddy Branch Rd., Gaithersburg, Md. 20760

[21] Appl. No.: 9,398

[22] Filed: Feb. 1, 1979

Related U.S. Application Data

[63] Continuation of Ser. No. 821,725, Aug. 4, 1977, abandoned.

[51] Int. Cl.² ............................................. G01N 23/20
[52] U.S. Cl. ..................................... 250/272; 250/273
[58] Field of Search ............... 250/272, 273, 274, 275, 250/505, 514

[56] References Cited

U.S. PATENT DOCUMENTS

| | | | |
|---|---|---|---|
| 3,833,810 | 9/1974 | Efanov | 250/273 |
| 3,961,186 | 6/1976 | Leunbach | 250/272 |

OTHER PUBLICATIONS

"Effective Elimination of the Compton Component in Amorphous Scattering by Experimental Means", Shimazu, Journal of Applied Crystalogray, 1974, 7, 531.

*Primary Examiner*—Craig E. Church
*Attorney, Agent, or Firm*—Howard L. Rose

[57] ABSTRACT

Method and apparatus for scanning an object, such as the human body, with radiation utilizes a slit for passing only a portion of scattered radiation from a radiation beam directed through the object to a radiation detector. The slit is arranged with its length extending transverse to the direction of the radiation beam such that the portion of scattered radiation passed by the slit is within a predetermined included angle, preferably within the range of from 60° to 120° and optimally 90°, to produce bands of scattered radiation lying within predetermined solid angles for detection and processing to provide a representation of the path of the radiation beam through the object. By scanning the object with a plurality of parallel radiation beams, which may be provided by translating the X-ray generator, a tomographic cross section of any desired configuration can be obtained.

22 Claims, 4 Drawing Figures

U.S. Patent
Oct. 21, 1980
4,229,651
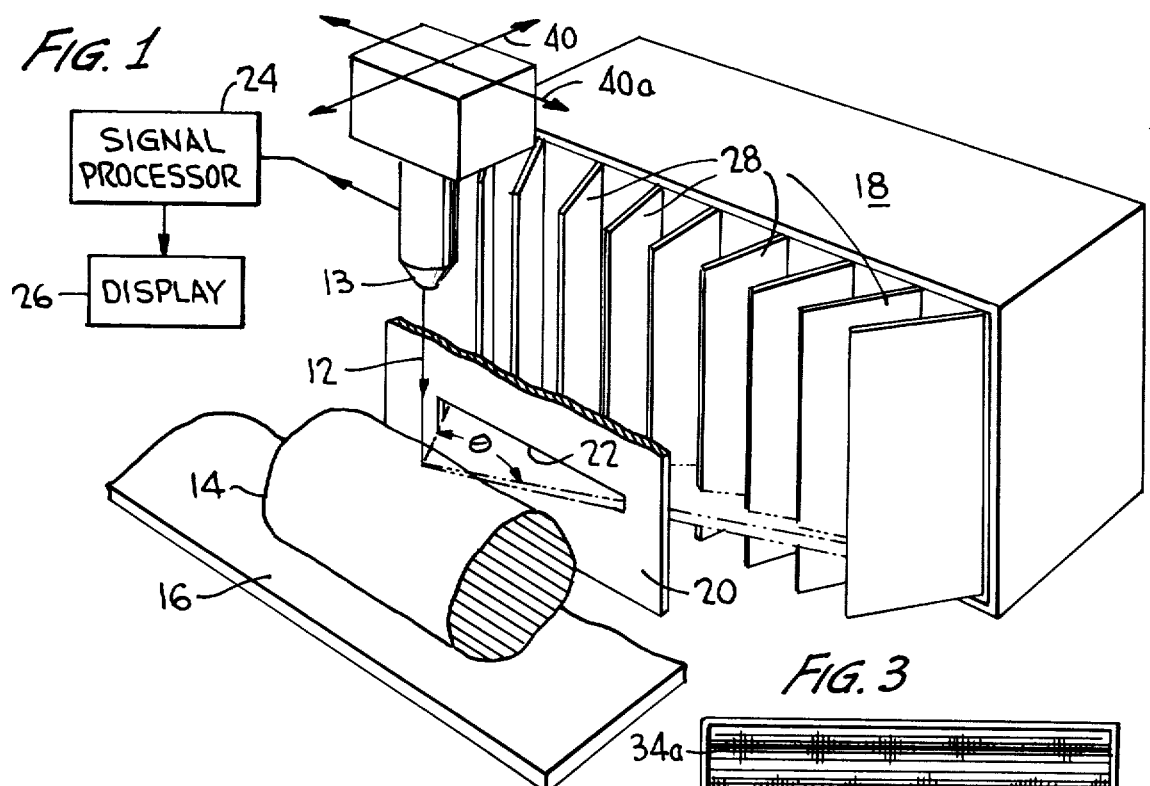
FIG. 1
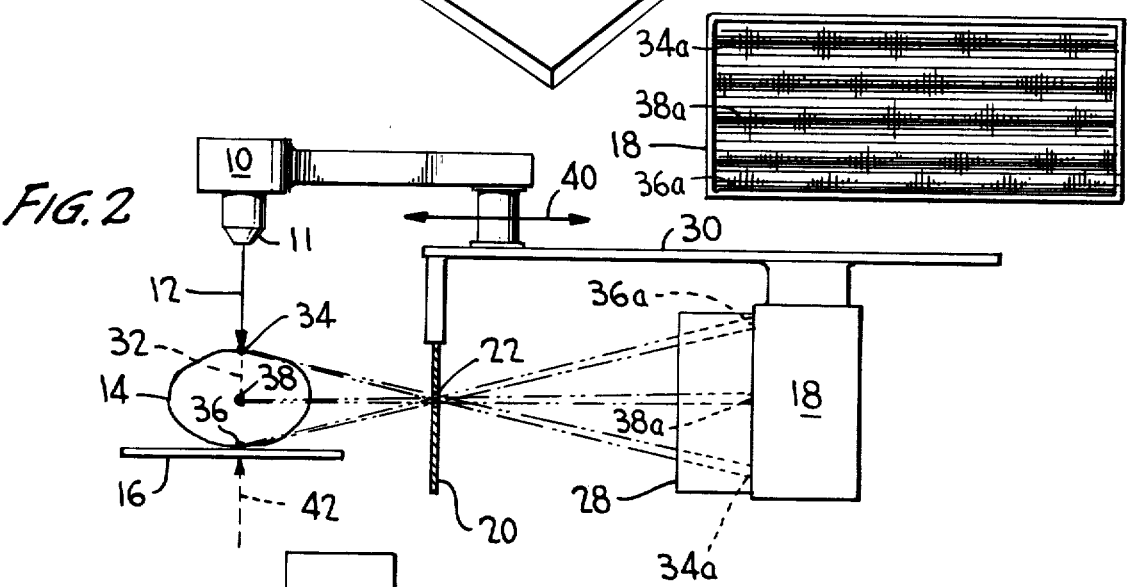
FIG. 2
FIG. 3
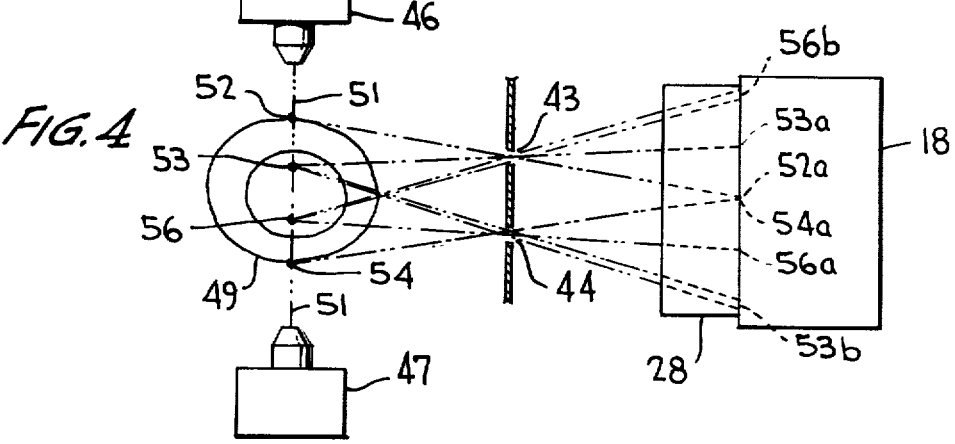
FIG. 4

RADIATION SCANNING METHOD AND APPARATUS

The Government of the United States of America has a nonexclusive, irrevocable, royalty-free license in the invention described herein with power to grant licenses for all governmental purposes.

This is a continuation, of application Ser. No. 821,725 filed Aug. 4, 1977.

BACKGROUND OF THE INVENTION

1. Field of the Invention

The present invention pertains to radiation imaging of objects and, more particularly, to method and apparatus for scanning an object with radiation beams to produce a tomograph of any arbitrary surface in the object by detecting only the radiation scattered along that surface.

2. Discussion of the Prior Art

Apparatus for producing tomographic cross sections of objects, such as the human body, utilizing radiation such as X-rays have in the past had the disadvantages of being extremely complex, expensive and confined to a plane perpendicular to the length of the beam. One reason for the complexity of prior art tomography apparatus is that they operate on the principle of transmissivity, that is the detection of radiation transmitted through an object, and therefore require the application of complex computer programs for implementing algorithms to obtain differential information relative to tissue and organs of the body. Another disadvantage of such tomography apparatus is that only planar, transverse cross sections can be obtained therewith thereby limiting the use of such apparatus and the information obtained during a scan.

SUMMARY OF THE INVENTION

Accordingly, it is an object of the present invention to overcome the above-mentioned disadvantages of the prior art by providing method and apparatus for radiation scanning which is relatively simple and inexpensive and can produce tomographic cross sections of any desired configuration.

A primary object of the present invention is to use scattered radiation from a radiation beam directed through an object to produce a visual display of the path of the radiation beam through the object.

Another basic object of the present invention is to use a slit to pass only a portion of scattered radiation occurring within a predetermined included angle to a radiation detector, the radiation being scattered from a radiation beam directed through an object. The predetermined included angle is preferably within the range of from 60° to 120° and is optimally 90°.

The present invention has a further object in that a tomographic cross section of an object can be obtained by scanning the object with a plurality of parallel radiation beams, provided for instance by translating the X-ray generator so that each incremental cross section of the object is viewed, detecting bands of scattered radiation within a predetermined angle from each radiation beam to produce electrical signals corresponding to the bands and accumulating and processing the electrical signals to provide a visual display.

An additional object of the present invention is to produce a solid angle of scattered radiation from each point along a line upon which a radiation beam is directed through an object to provide sufficient scattered radiation to permit its use in differentiating matter, such as tissues and organs, in radiation scanning.

Some of the advantages of the present invention over the prior art are that the different scatter characteristics for different tissues and organs of the human body permit simplified signal processing, the apparatus is simplified and can be moved for scanning along any arbitrary path thus producing tomograms along arbitrary cross sections and that low radiation beam strengths or dosages are required thereby permitting safe use for additional applications such as an adjunct in radiation therapy.

The present invention is generally characterized by radiation scanning apparatus including a radiation source for directing a radiation beam through an object to be examined and producing scattered radiation therefrom, a radiation detector positioned to detect the scattered radiation produced by said radiation beam, and a slit extending transverse to the direction of said radiation beam for passing a portion of the scattered radiation occurring within a predetermined included angle to said radiation detector whereby bands of scattered radiation are detected with each band being representative of a different point (small volume element, or area) along the path of the radiation beam through the object. The composite of the bands repressents the different incremental area (volume elements) along a single path, the band for each area providing a solid angle of scattered radiation sufficient to permit ready detection and visualization of each such area even though low levels of radiation are employed. The sensitivity of the apparatus also is such that soft tissue features may be detected. The present invention is further generally characterized by apparatus for detecting the bands of scattered radiation and producing electrical signals corresponding thereto, and successively processing the electrical signals representative of each parallel radiation path to provide a visual display of the cross section of the object being investigated.

Other objects and advantages of the present invention will become apparent from the following description of the preferred embodiment taken in conjunction with the accompanying drawings.

BRIEF DESCRIPTION OF THE DRAWINGS

FIG. 1 is a diagrammatic perspective view of radiation scanning apparatus according to the present invention.

FIG. 2 is a diagrammatic side elevation of the radiation scanning apparatus of FIG. 1.

FIG. 3 is a front elevation of the radiation detector of the radiation scanning apparatus of FIG. 1.

FIG. 4 is a diagrammatic side elevation of a modification of the radiation scanning apparatus of the present invention.

DESCRIPTION OF THE PREFERRED EMBODIMENT

Radiation scanning apparatus according to the present invention is illustrated in FIGS. 1 and 2 and includes a source of radiation 10 arranged to produce a narrow beam of penetrating radiation 12, such as X-radiation, via a collimator 13 directed through an object 14 such as a human body, positioned on a suitable support 16. The diameter of the X-ray beam 12 is desirably between 0.2 and 2 cm to provide both effective imaging and patient safety. Preferably, the X-ray beam is directed vertically at the object 14, and a radiation detector 18 is arranged in horizontally spaced alignment with the object to receive scattered radiation therefrom in a direction transverse to the radiation beam 12. A mask 20 is disposed in a vertical plane between the object 14 and the radiation detector 18 and has a slit 22 therein permitting scattered radiation to pass therethrough to be received at the radiation detector. The slit 22 has a width in the range of from 1 to 10 mm, preferably one-half the diameter of the X-ray beam 12 and has a length of approximately 20 cm such that the portion of the radiation scattered from a point in the object passed by the slit occurs in a predetermined included angle $\theta$, the included angle $\theta$ being preferably within the range of from 60° to 120° and optimally 90°. The center of the slit 22 lies along a perpendicular to the axis of the beam at the vertical center, as viewed in FIG. 2, of the object 14. The slit 22 is preferably positioned midway between the beam 12 and the radiation detector 18 such that the distance between the beam and the slit is equal to the distance between the detector and the slit.

The radiation detector 18 may be of any conventional type suitable to detect scattered radiation. For example, a tube may be used having a cesium iodide plate emitting light scintillations upon incidence of scattered radiation on the plate to provide a light signal for scanning parallel to the bands with a television camera. The signal from the television camera is processed in a signal processor 24, forming no part of the present invention, which can include a computer as well as other suitable processing circuits and equipment, or supply an information storage device and amplifiers, to produce a signal supplied to a display 26, such as a CRT, to provide a visual indication of the path of the radiation beam 12 through the object 14. Arranged between the radiation detector 18 and the mask 20 are a series of spaced baffles 28, such as Bucky baffles, each extending vertically along the face of the radiation detector and being radially aligned relative to the radiation beam 12 and in parallel relation therewith. The radiation source 10, radiation detector 18, mask 20 and baffles 28 are preferably mounted on a single support structure 30, as shown in FIG. 2, such that they are movable together as a unit for tomography scanning.

In operation, an object 14 is positioned on support 16, and the radiation source apparatus is positioned with the radiation source 10 above a portion of the object to be viewed. The X-ray beam 12 from source 10 passes vertically through the object along a line indicated by dashed line 32 in FIG. 2, and radiation is scattered from each point (small volume element or area) along the line 32, as indicated, for example, by points 34 and 36 near opposite sides of the object and point 38 near the center of the object. The radiation scattered from each point within the solid angle defined by the width and length of slit 22 and the distance between the slit and the X-ray beam 12 will be received by radiation detector 18 in the form of a band or strip extending horizontally across the face of the radiation detector. The strips 34a, 36a and 38a shown in FIG. 3 are representative of radiation scattered from points 34, 36, and 38, respectively; and, it will be appreciated that the entire face of the radiation detector receives bands of scattered radiation for corresponding points along line 32. That is, for any point along the line 32 of the beam passing through the object, the slit 22 will pass scattered radiation to produce rectangular line or image on the screen of the detector 18 corresponding to the radiation scattered from that point. The amount of scattered radiation passed by the slit is determined by the width of the slit which defines spatial resolution. Spatial resolution is also determined by the diameter of the beam 12 and, for optimum operation, the slit width is determined as a function of the beam diameter, the slit width being preferably one half the diameter of the beam. Due to the position of the slit 22 between the X-ray beam 12 and the radiation detector 18 the image of bands at the radiation detector is inverted relative to the corresponding points along line 32.

The baffles 28 eliminate background radiation due to their radial relationship with beam 12 that is, any radiation which is scattered from points not along line 32 will travel along paths not aligned with the baffles 28 and, thus, will strike the baffles to be absorbed or reflected such that the radiation will not be received by detector 18.

By scanning each band, the intensity of radiation scattered by each point can be determined from each band; and, since various types and densities of materials or tissues have various X-radiation scatter characteristics, the material nature of the object 14 can be displayed by an image on display 26. More particularly, relative to the human body, various types of tissue and organs have various scatter characteristics; and, thus, a picture of the body intersected by the X-ray beam 12 can be visually displayed. By moving the radiation scanning apparatus along a straight path, as indicated at 40, or a path of curved or other desired configuration, as indicated at 40a, for example, to scan the body with a plurality of parallel radiation beams and storing the signals from radiation detector 18 in memory, point by point for each X-ray beam, the signals can be accumulated and read out in proper order from the memory in signal processor 24 to produce a transverse or other desired configuration tomographic cross section of body 14 on display apparatus 26.

The X-ray dosage or beam strength required to produce a usable signal from radiation detector 18 is dependent upon the threshold of the radiation detection system and can be varied dependent upon the system threshold; however, the dosage required is, in any case, substantially less than the dosage required for transmissive X-ray tomography and scatter X-ray techniques that do not utilize the solid angle scatter employed herein. Accordingly, the radiation scanning apparatus of the present invention can be used with increased patient safety and for more applications than conventional transmissive systems. For example, the reduced X-ray dosage of the radiation scanning apparatus permits it to be used in conjunction with radiation thereapy equipment to provide a visual indication of the area being treated with radiation to assure precise positioning of the radiation thereapy equipment relative to the target. This can be used both during radiation treatment to monitor the position of the therapy X-ray beam with respect to the tissue to be irradiated as well as during the procedure of positioning of the beam with respect to the target prior to commencement of the treatment; for example, this preliminary alignment procedure can be carried out with a substantially reduced X-ray beam intensity so as not to expose the patient to unneeded radiation.

The display 26 can be provided with conventional controls to change threshold level, contrast, image size, brightness and the area or part of the object to which primary attention is to be directed. The resolution of the image on display 26, which is obtained from an accumulation of the scattered radiation detected from the X-ray beams generated in a scan across the object, is dependent upon the spacing between the X-ray beams and can be varied as desired. The storage capacity required in the signal processor 24 is necessarily a function of the resolution or number of beams per scan; and number of bands per scan; however, an 100 by 200 matrix core memory has been found to be acceptable for most applications.

As the X-ray beam 12 passes through the object 14, it is attenuated; that is, the intensity of the beam is reduced as it passes from point 34 at its entry into the object to point 36 at the opposite side of the object. If the beam intensity fall off distribution is known, the output from the radiation detector 18 can be weighted to compensate for the intensity fall off, such weighting being simply accomplished in the signal processor 24, such as by means a computer program relating scatter attenuation to position of a point within the object along the line 32. The intensity fall off can generally be characterized as a function of $e^{-x}$ where x is distance into the object of the X-ray beam.

Another approach to compensating for intensity fall off of the beam is to expose the object to a second X-ray beam 42 entering the object from the opposite side as shown in dashed lines in FIG. 2. With the X-ray beams 12 and 42 passing along line 32° from 180° positions, the intensity fall off distribution has a hyperbolic cosine configuration rather than the exponential fall off obtained with a single X-ray beam.

A plurality of radiation scanning apparatus according to the present invention can be utilized simultaneously, as shown in FIG. 4 and overlap of the bands representative of the central region utilized to further reduce attenuation effects. Specifically, the apparatus employs two slits 43 and 44, two X-radiation sources 46 and 47 and a radiation detector 18. The sources 46 and 47 direct radiation into object 49 coaxially from opposite directions along path 51. The body regions lying along path 51 between points 52 and 53 are imaged on the device 18 between points 52a and 53a thereon. The body regions lying between points 54 and 56 are imaged between points 54a and 56a. However, the body regions lying between points 53 and 56 are imaged along two different areas of the device 18, between points 53a and 56b, and between points 56a and 53b. Since the bands lying between these two sets of points represent the same information, arranged as mirror images on the detector, the electrical signals from each pair of the bands may be combined to represent a single unit of information. Attenuation effects are greatly minimized by this technique.

By using slit 22, the low intensity of scattered radiation, which would prevent the use of a pin-hole camera for radiation scanning, is overcome in that a solid predetermined included angle of scattered radiation is passed to the radiation detector 18 to form a band associated with each point along the path of the radiation beam through the object. To this end, the predetermined included angle used is dependent upon the soft tissue resolution desired; however, the predetermined included angle is optimally 90° and preferably within the range of from 60° to 120°.

While the scattered radiation has been shown as being detected along a path substantially transverse to the radiation beam, it will be appreciated that the scattered radiation could be detected along a path at any angle to the radiation beam due to the 360° nature of the scatter.

Although the apparatus of the present invention is described relative to use in the analysis of the human body, it has many additional uses in analysis of living tissue and in industrial applications. In the latter case the fact that the X-ray can be made from one side of a body is extremely useful in these applications where access to only one side of an object is available. Also the apparatus is useful in eliminating unwanted effects from certain types of analyses. For instance, defects in the wall of a filled large diameter oil tank can not be readily detected by conventional X-ray due to the X-ray absorbtion in such a large body of oil, i.e. the body is effectively too dense for normal X-ray equipment. The use of the apparatus of the present invention permits an operator to make such measurements since the scatter from the wall of the tank is available without attenuation by the oil; the apparatus only sees the wall.

While I have described and illustrated one specific embodiment of my invention, it will be clear that variations of the details of construction which are specifically illustrated and described may be resorted to without department from the true spirit and scope of the invention as defined in the appended claims.

What is claimed is:

1. Radiation scanning apparatus comprising
   radiation source means for directing a beam of X-radiation through an object to be examined to produce scattered radiation therefrom along the path of the beam through the object;
   radiation detector means positioned to detect scattered radiation produced by directing said beam of radiation through the object;
   a mask disposed between the object to be examined and said radiation detector means; and
   slit means formed in said mask and having its elongated dimension extending transverse to the path of the beam of radiation for passing through the mask to said radiation detector means that part of the radiation which is scattered from each point of the object along the path of the beam and which lies within a predetermined included angle;
   said elongated dimension of said slit means being substantially greater than the other dimension of said slit means;
   said detector means including means for examining bands of the scattered radiation passed through said slit means to produce signals representative of the scattered radiation in each band whereby the structure of the object lying along the path of the beam of radiation through the object may be determined.

2. Radiation scanning apparatus as recited in claim 1 wherein said slit means has a length and location between the object to be examined and said radiation detector means such that said predetermined included angle is within the range of from 60° to 120°.

3. The apparatus of claim 1 wherein said mask is disposed in a region midway between said beam and said detector means, and
   wherein said elongated dimension of said slit is at least ten times said other dimension of said slit.

4. The apparatus according to claim 1 wherein said slit means has a length and location between the object to be examined and said radiation detector means such that said predetermined angle lies in a range between approximately 60° and an angle greater than 90°.

5. Radiation scanning apparatus as recited in claim 1 wherein said slit means and said radiation detector means are positioned to detect scattered radiation extending along a path substantially transverse to said radiation beam.

6. Radiation scanning apparatus as recited in claim 1 and further comprising baffle means arranged between said slit means and said radiation detector means to prevent background radiation from being detected by said radiation detector means.

7. Radiation scanning apparatus as recited in claim 6 wherein said baffle means includes a plurality of baffles positioned in radial parallel relation with said radiation beam.

8. Radiation scanning apparatus as recited in claim 2 wherein said radiation detector means provides electrical signals corresponding to the bands of scattered radiation, said bands lying parallel to the elongated dimension of said slit means, and further comprising signal processing means for accumulating and processing said signals from said radiation detector means, and display means coupled with said signal processing means to provide a visual display of the path of said radiation beam through the object.

9. Radiation scanning apparatus as recited in claim 8 and further comprising support means for moving said radiation source means, said radiation detector means and said slit means together to permit scanning of the object with a plurality of parallel radiation beams; said signal processing means storing said electrical signals from said radiation detector means for each radiation beam and processing said electrical signals to provide visual display of a cross section of the object on said display means.

10. Radiation scanning apparatus as recited in claim 8 wherein said signal processing means includes means for weighting said electrical signals to compensate for attenuation of said radiation beam as said radiation beam passes through the object.

11. The radiation scanning apparatus of claim 1 wherein said slit means includes a plurality of parallel spaced slits arranged in a plane parallel to said radiation beam.

12. The apparatus according to claim 1 wherein said beam is a pencil beam.

13. Radiation scanning apparatus as recited in claim 12 wherein said predetermined included angle is 90°.

14. Radiation scanning apparatus as recited in claim 13 wherein said slit means has a width of from 1 to 10 mm.

15. The radiation scanning apparatus of claim 12 wherein said slit means is disposed midway between said radiation beam and said radiation detector means and has a width one half said diameter of said radiation beam.

16. The apparatus of claim 15 wherein said elongated dimension is at least an order of magnitude greater than said other dimension of said slit means.

17. The radiation scanning apparatus of claim 12 further comprising additional radiation source means for directing a second radiation beam through the object, from a direction opposite said first mentioned radiation beam.

18. A method of radiation scanning for producing an image of the internal structure of an object along a pencil beam of radiation comprising the steps of:

directing a beam of X-radiation along a path through the object to produce scattered radiation from each point of the object along the path of the beam;

locating along a path perpendicular to the beam a means having the characteristics of an optical slit sufficiently narrow in its dimension parallel to the axis of the beam to have the effect of an image forming aperture and a dimension perpendicular to the axis of the beam substantially wider than the narrow dimension of the slit;

passing the scattered radiation through the means to establish in a plane in space parallel to the axis of the beam, an array of scattered radiation reversed in positions relative to their points of origin along the axis of the beam and subtending a wide angle of scattered radiation perpendicular to the beam from each point along the beam;

successively detecting contiguous narrow elongated bands of the array of scattered radiation perpendicular to the axis of the beam at the plane in space, the bands each being delimited by a solid angle defined solely by the dimensions of the means and its spacing from the object; and producing discrete signals corresponding to the radiant energy in each band.

19. The method according to claim 18 further comprising processing the electrical signals produced from each band to provide an image of the object along the path.

20. A method of radiation scanning as recited in claim 19 wherein said step of directing a radiation beam includes directing a plurality of parallel radiation beams at the object, said step of passing scattered radiation and said step of detecting the scattered radiation are repeated for each radiation beam, and said step of processing the electrical signals includes accumulating and processing the electrical signals produced for each radiation beam to provide a visual display representative of a cross section of the object.

21. The method of claim 19 comprising the further steps of investigating adjacent contiguous parallel paths through the object, and combining the signals produced by the totality of signals produced by successive beams to produce a cross-sectional view of the object.

22. Apparatus for producing cross-sectional X-rays of human bodies comprising

A source of X-radiation for forming a pencil beam of radiation;

means for directing said pencil beam sequentially and successively through contiguous regions of the body to produce scattered radiation from each point of the body to be investigated;

radiation detector means positioned to detect scattered radiation produced by directing each said pencil beam of radiation through the object;

aperture defining means disposed between the object to be examined and said radiation detector means defining a slit having its elongated dimension extending transverse to the axis of said pencil beam of radiation for passing to said radiation detector means that part of the radiation which is scattered from each point of the object along the path of said pencil beam and which lies within a predetermined solid angle defined solely by the position of said slit relative to the object and by the dimensions of said slit;

said elongated dimension of said slit being at least an order of magnitude greater than the narrow dimension of said slit;

said detector means including means for examining bands of the scattered radiation passed through said aperture defining means to produce signals representative of the scattered radiation in each band whereby the structure of the object lying along the path of the beam of radiation through the object may be determined.

* * * * *